US006344741B1

United States Patent
Giguere et al.

(10) Patent No.: US 6,344,741 B1
(45) Date of Patent: Feb. 5, 2002

(54) PULSED EDDY CURRENT METHOD FOR DETECTION OF CORROSION IN MULTILAYER STRUCTURES USING THE LIFT-OFF POINT OF INTERSECTION

(75) Inventors: Sylvain Giguere, Orleans; Stéphane J. M. Dubois, Kingston, both of (CA)

(73) Assignee: Her Majesty the Queen as represented by the Minister of National Defence in right of Canada, Ottawa (CA)

( * ) Notice: Subject to any disclaimer, the term of this patent is extended or adjusted under 35 U.S.C. 154(b) by 0 days.

(21) Appl. No.: 09/597,221

(22) Filed: Jun. 20, 2000

(51) Int. Cl.[7] .............................................. G01N 27/82
(52) U.S. Cl. ...................... 324/240; 324/225
(58) Field of Search .................. 324/240, 225, 324/228, 229, 242, 243, 232, 233, 260, 238, 639

(56) References Cited

U.S. PATENT DOCUMENTS 4,383,218 A * 5/1983 Hansen et al. ............... 324/225
4,929,898 A * 5/1990 Spies .......................... 324/242

* cited by examiner

*Primary Examiner*—Safet Metjahic
*Assistant Examiner*—Subhash Zaveri
(74) *Attorney, Agent, or Firm*—Larson & Taylor, PLC

(57) ABSTRACT

A method for the detection and the characterization of corrosion in multi-layer metallic structures using a pulsed eddy current technique. For this technique, a coil (or coils) is used both as field source (driven by a square wave voltage-controlled excitation), and/or as field sensor (measuring a transient response). The field sensor allows the capture of information about the condition of the area of the structure under inspection. The ability of this technique to detect corrosion hinges on the use of a transient response feature (i.e., Lift-off Point of Intersection) to infer the presence of material loss. With the help of a calibration standard, the Lift-off Point of Intersection provides the ability to quantify material loss in multi-layered structures. The results obtained with this method are independent of lift-off variations inherent to field inspections (i.e., changes in distance between the transducer and test object).

18 Claims, 6 Drawing Sheets

PULSED EDDY CURRENT METHOD FOR DETECTION OF CORROSION IN MULTILAYER STRUCTURES USING THE LIFT-OFF POINT OF INTERSECTION

FIELD OF THE INVENTION

The present invention relates, in general, to the detection and characterization of defects in metal structures and, in particular, to a method for determining the structural integrity of multi-layer structures such as an aircraft fuselage lap splice.

BACKGROUND TO THE INVENTION

Corrosion is a major problem that can compromise the structural integrity of equipment in many diverse industries such as in pipelines (gas or oil) or in the aircraft industry. In the aircraft industry, this situation is a primary concern to the engineering authority responsible for aircraft airworthiness. One structure closely scrutinized in the aircraft industry is the fuselage lap splice. This metallic multi-layer structure has a design such that a crevice exists where conditions are favourable for corrosion. Corrosion in a lap splice could, ultimately, lead to a structural failure of the fuselage.

Visual inspection is one method for detecting corrosion in multi-layer structures such as in aircraft fuselage lap splices. This technique is based on the principle that, when corrosion takes place between the layers, the metal lost to corrosion results in a product that forces the plates apart and causes surface distortion. The visual inspection, however, does not provide a fool proof indication that the deformation is actually due to corrosion. Such distortion may exist, for example, as a result of poor quality control during manufacturing or from a previous repair. Ultrasonic techniques have also been used to detect corrosion in metal pipes such as the techniques described by David Wang in Canadian Patent Application 2,258,439. The detection of defects, other than those in the first layer, using ultrasonic techniques requires a mechanical bond between plates. The absence of a bond will preclude detection in second, third or fourth layer defects.

Another method for detecting corrosion in metal 10 structures is the use of a low-frequency eddy current inspection method. A low-frequency eddy current inspection technique uses a coil to induce eddy currents in a test object. The induced eddy currents produce a time-varying magnetic field which can be measured by magnetic flux sensors to yield information about the condition of that test object and determine whether a loss of material due to corrosion has occurred. A low-frequency eddy current inspection method can detect a loss of material in a metallic structure but is not always reliable. It often requires the use of dual frequency methods and signal mixing to detect corrosion.

Canadian Patent 2,102,647 by John H. Flora et al is directed to detecting defects in a metal component using a low frequency eddy current technique. John H. Flora et al uses an excition coil wound on a yoke and a pair of magnetic flux sensors differentially connected with respect to each other in an area under the yoke. The differential connection will result in the cancellation of common signals detected by the sensors, those which would be generated by the coil, but allow the detection of other signals generated by eddy currents in the metal component. The yoke is then placed near the metal component and a low frequency alternating current applied to the coil to generate eddy currents in the metallic component, which currents are detected by the sensors. The yoke is moved along the surface to scan for defects by changes in the generated eddy currents at defect locations.

U.S. Pat. No. 4,843,319 by Pedro F. Lars and U.S. Pat. No. 4,843,320 by Brian R. Spies are directed to corrosion detection where a transmitting antenna coil is placed next to a metal container, in this case a pipe with layer of insulation on it, and applying a train of pulses to that transmitting coil. The pulses are shaped so the coil is energized for a sufficient period of time to stabilize the magnitude of the field, with no eddy current then being generated, and then de-energizes abruptly to generate eddy currents in the metal which are detected by a receiving coil. Those eddy currents decay and are gradually dissipated within the metal with the rate of diffusion being dependent on the conductivity and thickness of the metal. The decay of those eddy currents is detected by a receiving coil and used to determine if defects in the metal exist such as caused by corrosion and a resulting change in thickness of the metal. However, errors in responses will occur due to variations in distance between the antenna and the metal wall of the container. Pedro F. Lara discusses some methods for correcting those errors in responses. The pulses used in these US Patents operate in the time domain rather than in a frequency domain manner as used in Canadian Patent 2,102,647. In the time domain, the information needed to probe a conductor wall for reasonably accurate detection can be obtained with one transmitted pulse. Each pulse contains an infinite number of frequencies. In frequency domain methods, however, only a few frequencies are used to probe a conductor wall which results in a limited amount of information from which the wall thickness is to be determined.

U.S. Pat. No. 6,037,768 by John C. Moulder et al describes another pulsed eddy current (PEC) apparatus to detect corrosion in metal structures such as aircraft lapjoints. John C. Moulder et al describes a calibration of the PEC instrument before the inspection with a reference structure that the user knows to be flaw-free. The PEC probe, once calibrated, scans in serpentine fashion a selected fashion area under computer and motor driven control. John C. Moulder et al indicates in lines 38 to 44 of column 4 that an air gap between the probe and lapjoint is known as "lift-off" and that ideally, lift-off remains constant at 0.007 of an inch during a scan since the probe has a constant built-in wear surface. However, possible irregularities in a lapjoint surface may result in greater lift-off with a possibility of obtaining anomalous inspecting result. The user, during a scan is, however, able to filter from the display known conditions such as the existence of fasteners and airgaps and excessive probe lift-off.

Prior art methods of detecting corrosion in aircraft lap splices multi-layer metallic structures have proven inadequate. The detection of corrosion by either ultrasonic or eddy current techniques is not inherently difficult, but, there are problems with the identification and characterization of that corrosion due to the complexity of multi-layer structures. To quantify the thinning in multi-layer structures, it is required to determine in which layer corrosion has occurred. Ultrasounds, for instance, will not easily penetrate beyond the first layer. Eddy current techniques, on the other hand, have the ability to perform multi-layer inspections without requiring a mechanical bond. Notwithstanding these limitations, most operators have elected to conduct visual inspections followed by low-frequency eddy current inspections to detect corrosion in aircraft lap splices. This approach reduces the number of false indications but it is not capable of isolating corrosion below 10% thinning in the first layer. Further, second and third layer corrosion may also progress to much greater amounts of thinning before they are finally detected by this approach.

SUMMARY OF THE INVENTION

It is an object of the present invention to provide a pulsed eddy current method for detecting defects in a metallic structure and allow a quantitative evaluation of any defects detected.

A method for detecting defects in a metallic structure, according to one embodiment of the present invention, comprises locating a transducer at a first distance from said metallic structure at one area that lacks any significant defects in the structure, activating said transducer with a square wave voltage controlled excitation to generate eddy currents in the structure and then sensing, with at least one magnetic flux sensor, time-varying magnetic fields generated by the transducer and said eddy currents, signals obtained from said at least one sensor being recorded, this process being repeated to obtain at least one other recorded signal that is obtained with the transducer being locating in the same location but at a different lift-off distance from said one area, determining where the recorded signals cross to establish a Lift-off Point of Intersection at a point in time, placing said transducer at other areas of said structure which are to be tested for defects, activating said transducer with similar voltage-controlled excitation as applied at said one area, then obtaining and recording signals sensed from the time-varying magnetic fields generated by the transducer and eddy currents in a similar manner as at said one area, comparing the recorded signals amplitudes which are obtained at said other areas at said point in time with those of signals obtained at said one area with differences in signal amplitude providing indications of any defects present at areas being tested.

BRIEF DESCRIPTION OF THE DRAWINGS

The following detailed description of the invention will be more readily understood when considered in conjunction with the accompanying drawings in which.

DESCRIPTION OF THE PREFERRED EMBODIMENTS

Figure 1:
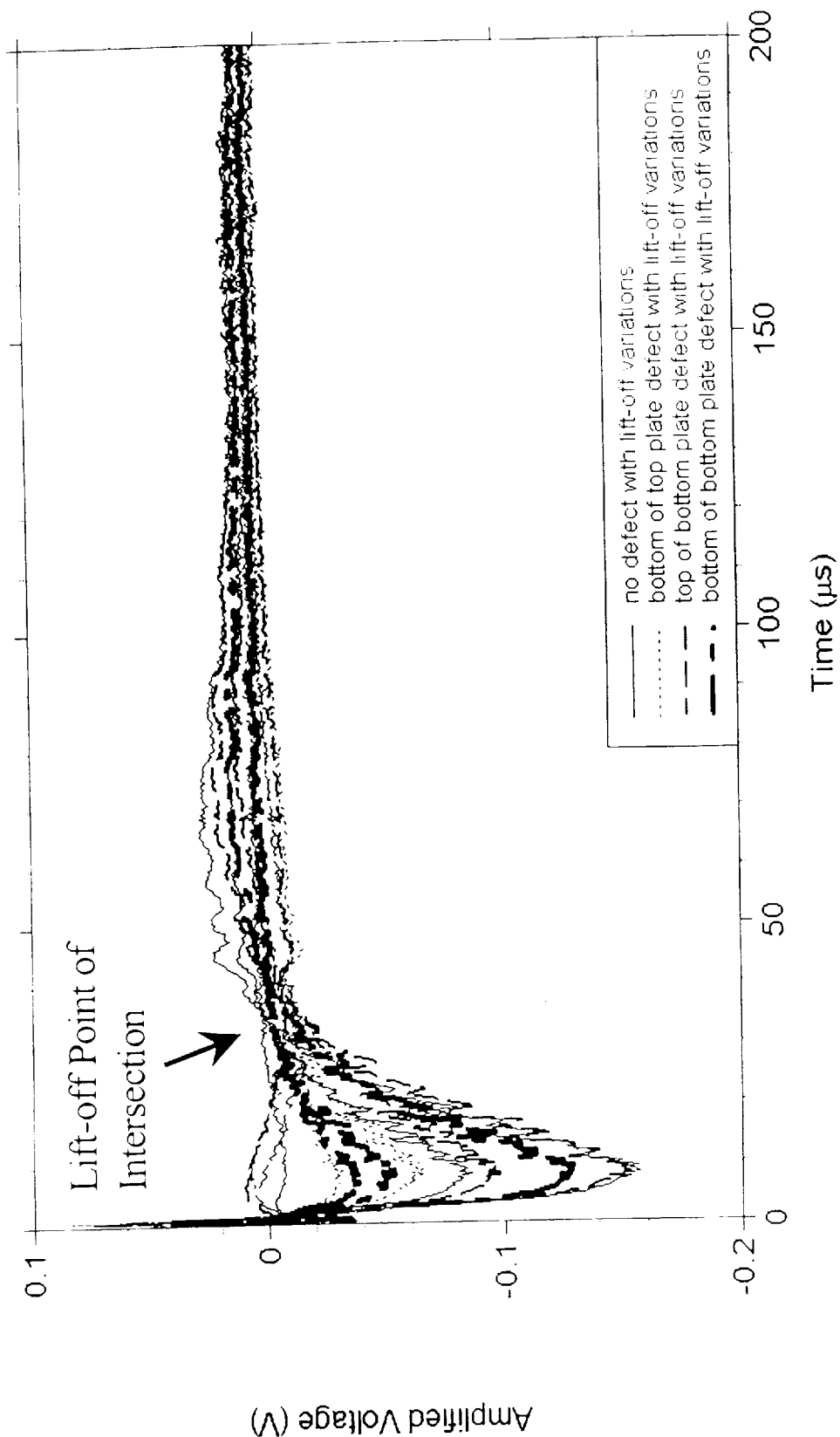
FIG. 1 is a composite graph of signals showing the effects of lift-off (the distance between the transducer and test object) on balanced transient responses for a single coil transducer.

Corrosion is a major problem that can compromise the structural integrity of equipment in diverse industries, such as pipelines or in the aircraft industry. In the aircraft industry, for example, corrosion is a primary concern for the engineering authority responsible for airworthiness with fuselage lap splices, in particular, requiring close scrutinization. Fuselage lap splices have a multi-layer metallic structure such that a crevice exists where conditions are favourable for corrosion and this corrosion, if it exists, could eventually lead to a structural failure of the fuselage.

One method for detecting corrosion in aircraft fuselage lap splices is by visual inspection. This technique is based on the principle that, when corrosion takes place, the metal lost to the corrosion forms a product that forces the multi-layer plates apart and causes surface distortion. Visual inspection, however, does not provide a fool proof indication that the deformation is actually due to corrosion. Distortion could also exist as a result, for example, of poor quality control during manufacturing or from a previous repair.

A low-frequency eddy current inspection method is another technique to detect corrosion in metal structures. In this technique, a transmitting coil is used to induce eddy currents in a metal structure. Those induced eddy currents produce a time-varying magnetic field that can be measured by magnetic flux sensors to yield information about the condition of the metal structure and provides an indication as to if any corrosion has occurred. This technique, however, is not always reliable and often requires the use of dual frequency methods and signal mixing to detect corrosion.

Another technique to detect corrosion is to apply a train of pulses to a transmitting antenna coil which is located near a metal structure and to measure the magnitude of fields generated by eddy currents produced in the metal structure by those pulses. U.S. Pat. No. 4,843,319 by Pedro F. Lars and U.S. Pat. No. 4,843,320 by Brian R. Spies describe such methods for detecting corrosion using pulses to induce eddy currents in pipelines for transporting oil or gas. The pulses applied to the transmitting coil in these U.S. Patents are shaped so the coil is energized for a sufficient period of time to stabilize the magnitude of the field, with no eddy current then being generated, and then de-energizing the coil abruptly to generate eddy currents in the pipeline which are detected by a receiving coil. The generated eddy currents decay and are gradually dissipated within the metal with that rate of decay being dependent on the conductivity and thickness of the metal in the pipeline at the area where those eddy currents were generated. The fields generated by the decaying eddy currents are detected by a receiving coil and that information is used to determine if defects in the metal exists such as those caused by corrosion and a resulting change in the thickness of the metal. Errors, however, will occur due to variations in distance between the antenna and metal wall of the pipeline. Pedro F. Lava discusses some methods for correcting those errors.

The detection and characterization of corrosion in multi-layer structures according to the present invention is carried out with a pulsed eddy current technique. Generally pulsed eddy current techniques, up to present, have attempted to keep the distance between the transmitter/receiver coils and the metal surface as constant as possible in order to avoid errors caused by variations in that distance to the data collected and to simplify the analysis of that data. It has been found, however, that when transmitter/receiver coils (transducers) are used in pulsed eddy current techniques, the transient responses for various lift-off distances (i.e. distance between the transducer and test object) intersect at a given point (i.e. Lift-off Point of Intersection) when no corrosion is present. This Lift-off Point of Intersection can then be used for the characterization of corrosion and, most importantly, the results obtained with this method are independent of lift-off variations inherent to field inspections.

The essence of a pulsed eddy current test is that current pulses drive a test coil assembly whose output signals are analyzed. The system's architecture is, up to a certain level, dictated by the transient response. Variations in the transient response due to defects are so small and the phenomenon occurs so rapidly that digital data processing generally is the only viable option. An enormous amount of digital data can be generated for a scan of a given surface. The analysis of that amount of digital data would require a microcomputer's data handling capability. A microcomputer can also be used to carry other functions such as:

a. controlling most of the parameter settings for the instruments;

b. reading and analysing the outputs of the eddy current instrument; and c. sending outputs to external equipment.

An architecture that could be selected to carry these functions is the star structure when the central unit of the system's architecture is the computer. External equipment would include the scanning system, the pulse generator and the inspection probe with each instrument being individually connected to the central control unit. The computer is the central control unit of this type of set-up and it is via one of its applications that the excitation is digitally triggered at given spatial positions during the scan of the test object. When a selected position for the test coil is reached, the computer sends a trigger to the pulse generator to provide the test coil assembly with the voltage controlled excitation signals.

The pulsed eddy current technique is based on the principle of magnetic induction where a transmitter coil (transducer) provides a magnetic field when excited with a square wave current (pulse) and this generates eddy currents in an adjacent metal structure (test object) to produce a magnetic field which opposes the field generated by the coil. The square wave produces a time-varying magnetic field and provides for a wide range of frequency excitation. The induced eddy currents flow at specific depths within the test object and decay over a period of time after the magnetic field being generated by the transducer is terminated. Various sensors can be used to capture the time-domain variations of the magnetic flux. Some sensors will measure the magnetic flux density while others will measure the rate of change of the total magnetic flux. Coils have the advantage to be the sensor mostly used for in-service applications.

The captured transient response in the time domain, also called A-scan, contains a broadband spectrum of excitation frequencies that, theoretically, can be analyzed to determine the test object condition, i.e. defect depth, size and location. The transient response also contains a large number of separate components (also transients) from different parts of the structure being investigated with many of those remaining constant. The major part of the total transient are, in fact, due to the field in air and the scattered field due to the specimen. The total transient can be subtracted in order to enhance the appearance of the small transients by a process referred to as a balancing process. The balanced transient is the traditional means used to determine the presence, the amount, and the location of corrosion. There is a significant drawback, however, to the balancing process with standard pulse eddy current techniques. In order to identify the flaw transient, the background parts of the transient must remain constant throughout the duration of even the most extensive of measurements. Any changes to the background such as lift-off, will be interpreted as changes to the flaw transient signal thus leading to inadequate interpretation of the responses received. Specifically, lift-off increases the balanced transient peak amplitude, advances its location and advances the time to zero crossing (where applicable) to such an extent that the defect's size and location cannot be adequately determined by traditional techniques.

The shape of the time-domain balanced transient responses sensed by magnetic field sensors changes tremendously with variation of distance between the transducers/sensors and test object, i.e. the lift-off distance. One particular feature, referred to as the Lift-off Point of Intersection, however, does not vary significantly with variation in lift-off distances and this feature can be used to provide a qualitative and quantitative evaluation of the extent of the corrosion in a given test object.

Determining a Lift-off Point of Intersection for a test object is relatively simple. A representative area of the structure without any defects is first selected to be inspected by the pulsed eddy current techniques described above in order to provide calibration curves of signals (responses) detected by the transducer or sensors due to the eddy currents generated. For that given calibration location, at least two but preferably three transient responses are recorded where only the transducer (or sensors) distance from the structure is varied, i.e. where only the lift-off distance is varied. The time at which the two or three lift-off balanced transient responses intersect is the Lift-off Point of Intersection. That time will be the same for any Lift-off the structure where defects might be present. If no significant defects are present in an area being tested at the Lift-off Point of Intersection, then the voltage amplitude of responses at that particular time will be close to zero for the referenced subtracted signals. The responses recorded at that point of time when other areas are being tested can then be evaluated to determine if any defect is present and the extent of that defect. Depending on the amount of material loss, the voltage amplitude of signals recorded at a test area will vary and this will provide a means to provide a quantitative evaluation of the material loss at that area. Effectively, the use of a calibration standard will allow the determination of material loss. It should be noted that the Lift-off Point of Intersection also exists for the transient responses before the reference substraction. Reference substraction is, therefore, not absolutely necessary.

The signal display is the real link between the test equipment and its intended purpose, i.e. detection and identification of corrosion. The transient response, as previously indicated, is a signal in the time domain and each point in the surface scan has a particular transient response. This situation limits the ability to assess the conditions of the test object. Advanced imaging and image enhancement software are generally used to provide a reasonable data interpretation capability. This will make it possible to represent the test object with a C-scan using only one feature of the transient response, e.g. the Lift-off Point of Intersection.

One type of transducer used to test a metal plate with the pulse eddy current technique was a single coil where the excitation and the sensing is carried out by the same coil. The single coil used for the first tests had an inside diameter of 6.6 mm, outside diameter of 13.9 mm a length of 0.685 mm and a wire gauge 41 AWG. Different size coils could be used and, effectively, a higher sensitivity could theoretically be achieved by building a larger inducing coil as this would allow for a higher depth of penetration of the magnetic fields. If, however, the same large coil is used for detection purposes, a low resolution and sensitivity would be achieved. The reason for this is that the coil would respond to all magnetic flux lines passing through the coil winding, regardless of the spatial direction and orientation. This, together with the size of the coil can impact on the sensitivity of sensor. Using a smaller coil would provide a better sensitivity but would limit eddy current penetration within the test object. Separate coils can be used to provide the excitation and the sensing.

One setting of particular interest is the pulse width. The selected width must be sufficient to allow the single coil transient response to reach its maximum and subsequently decrease to zero. Valuable information about the test sample may be lost if the width is inadequate to allow this to occur. There is also a requirement to determine an adequate sampling rate for a given transient response. A higher sampling rate gives more data points per unit of time and therefore produces improved accuracy in representing the original signal. The sampling rate should be at least twice the highest frequency measured.

The inspection of any test object is best accomplished with the help of a scanning system. In an experimental set-up for testing, the test sample was kept stationary and a scanning system alters the position of the transducer to cover the surface of the test sample. The operation of the scanning system is controlled by commands from the central computer having pre-selected parameters such as the scanning and index axis, the dimension of the area to be scanned and the scanning speed.

Figure 2:
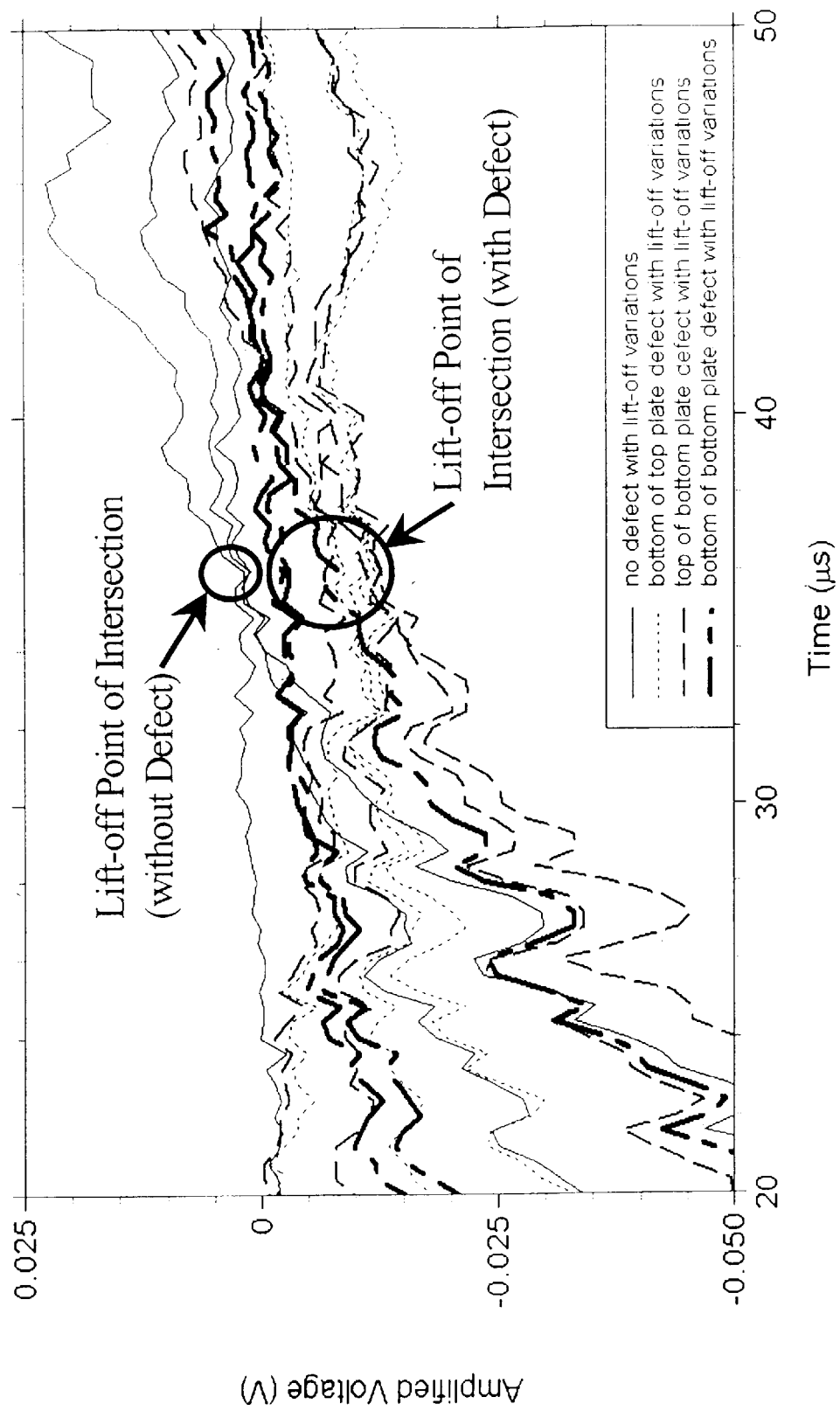
FIG. 2 is an expanded view of FIG. 1 near the Lift-off Point of Intersection.

A multi-layer structure was first tested with no lift-off and at areas where no defects were present to obtain a reference signal subsequently subtracted from all other transient responses. Then, the single coil transducer was positioned at various distances from the plate in order to determine a Lift-off Point of Intersection as illustrated by balanced transient response curves 1, 2 and 3 in FIG. 2, FIG. 2 being an expanded view of FIG. 1 near the Lift-off Point of Intersection in order to more clearly illustrate the balanced transient response curves at that area. In this case, with this particular metal plate structure, the time where the measured voltage amplitude of the three balanced transient responses intersect (the Lift-off Point of Intersection) was about 36 $\mu$s. That metal plate was then tested at other areas where known defects with a 14.4% material loss were present. The responses obtained were recorded and are shown in FIG. 1 and the expanded view of FIG. 2. The separation between the obtained signals at areas where defects are present and an area where no defect was present at the Lift-off Point of Intersection are clearly illustrated by these curves. In FIGS. 1 and 2 the plate was tested at an area where the 14.4% material loss defect was present at the bottom of the top plate, at an area where the defect was present at the top of the bottom plate and at an area where the defect was present at the bottom of the bottom plate. These are identified in FIG. 2 by the various types of lines representing the different response curves.

Figure 3:
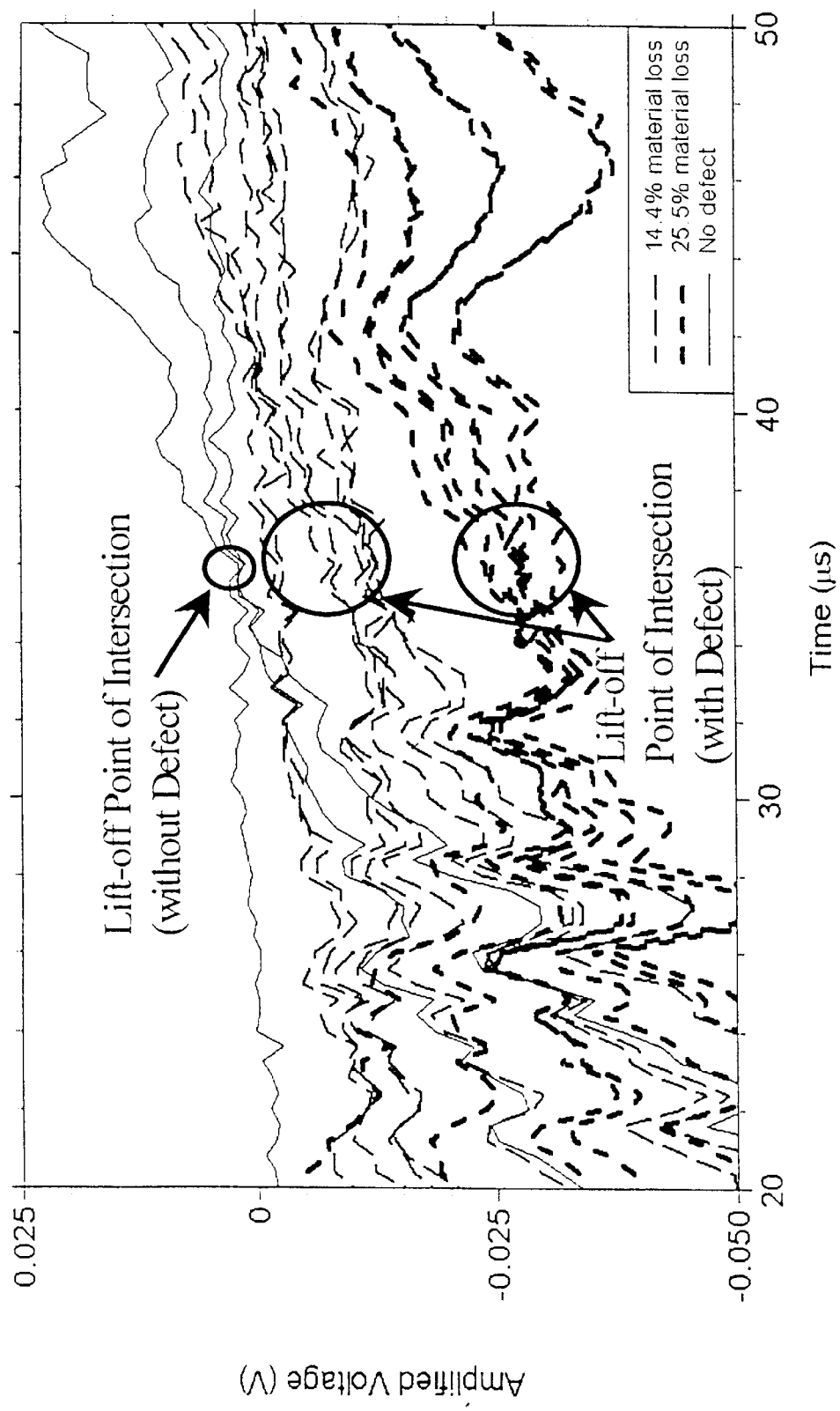
FIG. 3 is a composite graph of signals at the Lift-off Point of Intersection and illustrates the ability of the present invention to quantify material loss independently of lift-off variations using a single coil transducer.

The Lift-off Point of Intersection value (about 36 $\mu$s) is identical for each curve in FIG. 2 and the signal is almost zero when no defect is present as shown by curves 1, 2 and 3 at the Lift-off Point of Intersection. It is possible to ascertain the presence of corrosion in a multi-layer structure independently of lift-off variations from the separation between the curves at the Lift-off Point of Intersection located near 36 $\mu$s. The curves in FIG. 2 only highlight the ability to determine the presence of corrosion. The Lift-off Point of Intersection, however, also provides the ability to quantify the amount of material loss in a multi-layer structure. A variation in the material loss will translate into a variation of the voltage amplitude of responses at the Lift-off Point of Intersection and this is illustrated in FIG. 3. The lift-off Point of Intersection was determined to be around 36 $\mu$s, similar to that in FIGS. 1 and 2. The middle group of curves at the Lift-off Point of Intersection were obtained at an area of the metal plates where a 14.4% of material loss existed while the lower group of curves were obtained at an area where a 25.5% material loss existed. It is possible, as illustrated in FIG. 3, to quantitatively evaluate the amount of corrosion (or material loss) by using a calibration specimen to ascertain the voltage amplitude associated with a given loss of material.

Figure 4:
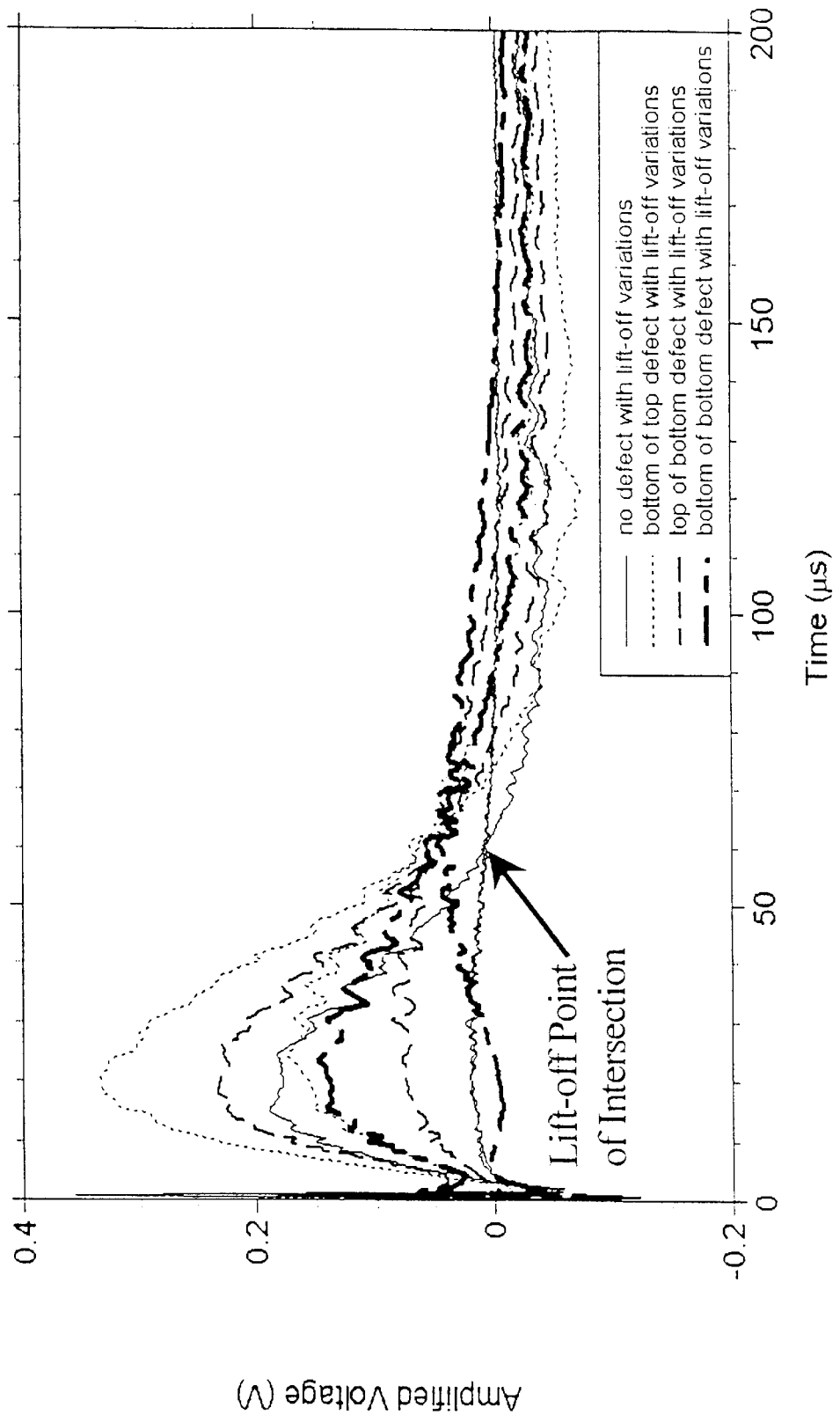
FIG. 4 is a composite graph of signals that illustrates the effect of lift-off on balanced transient response for a driver-pickup transducer and the separation of signals at an area with defects and one without defects.
Figure 5:
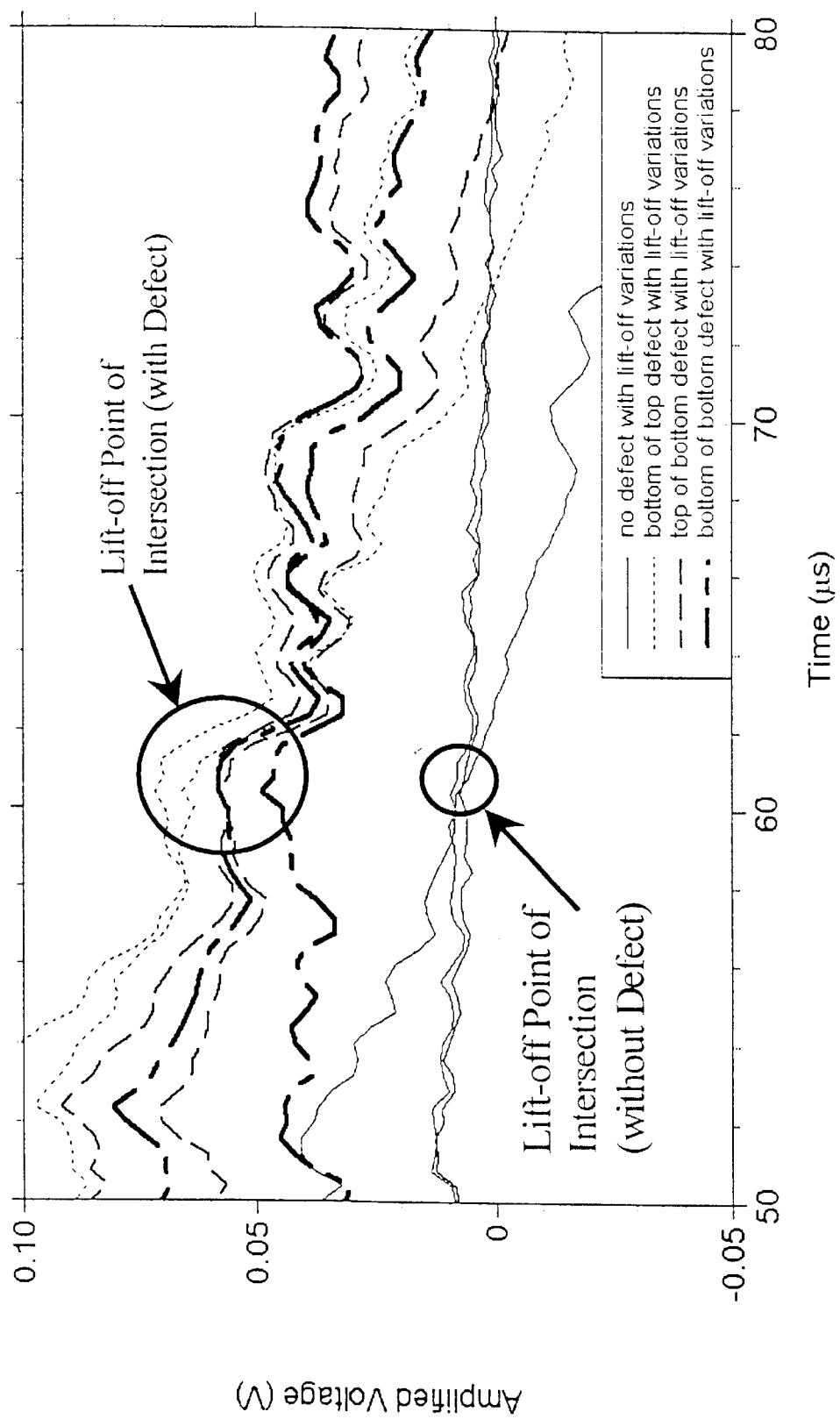
FIG. 5 is an expanded view of FIG. 4 near the Lift-off Point of Intersection.

Further tests were made on the structure with another type of transducer, a driver-pickup transducer. With this type of transducer, the excitation and sensing are carried out by two coils having different characteristics. The driver-pickup transducer configuration used for these tests consisted of two concentric coils with an excitation coil having the same dimensions as the single coil transducer. The detection coil had an inside diameter of 1.59 mm, an outside diameter of 6.35 mm, a length of 0.660 mm and a wire gauge 45 AWG. The testing and analysis carried out using this transducer followed the same procedure as previously done with a single coil. FIG. 4 shows a number of balanced transient responses combining flaw locations and lift-off distances obtained with the driver-pickup transducer. FIG. 5 is an expanded view of FIG. 4 at the Lift-off Point of Intersection area. This figure clearly shows the separation between the curves at the Lift-off Point of Intersection at an area where no defects were present (calibration curves) and at areas where defects are located.

Figure 6:
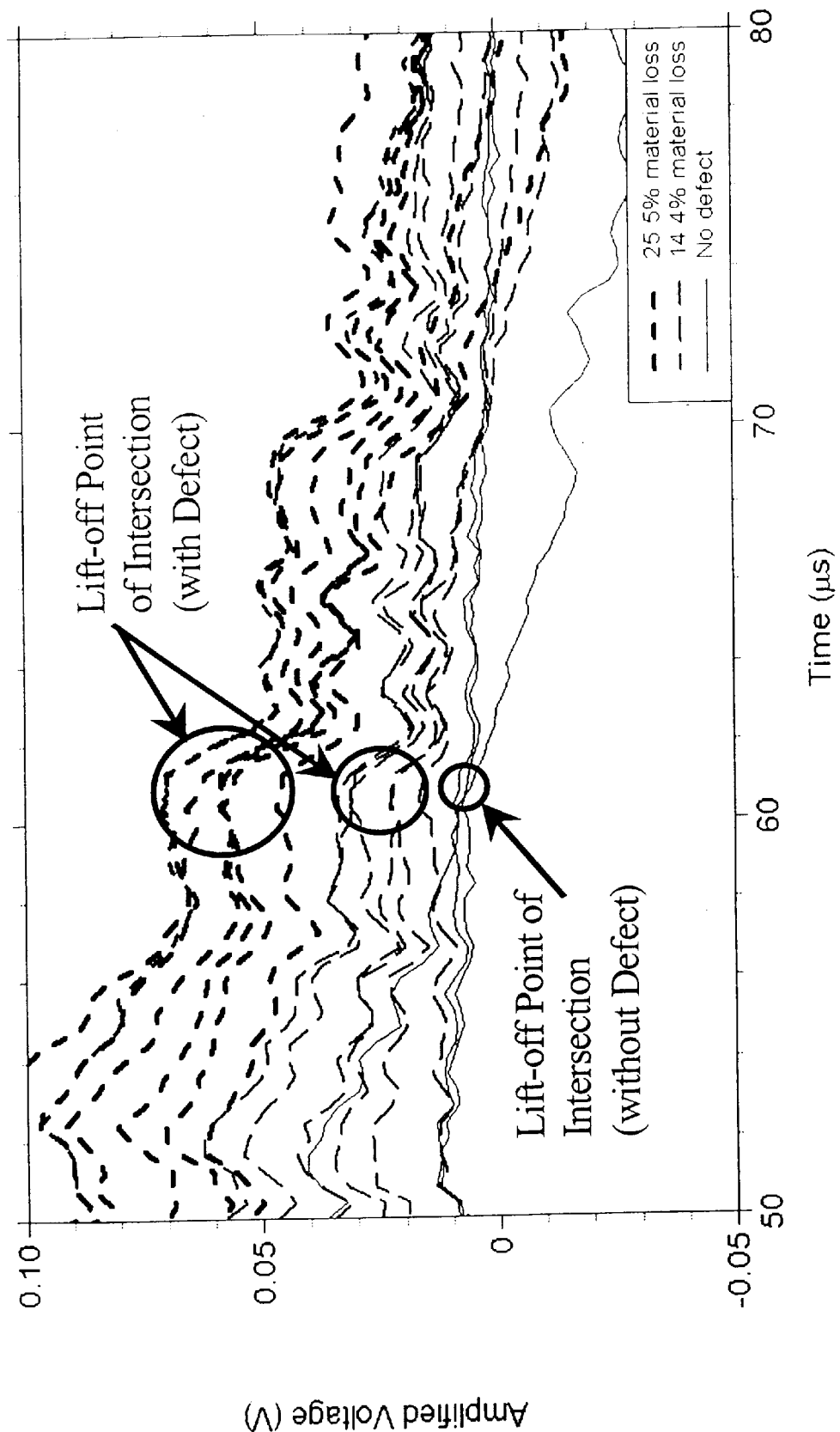
FIG. 6 is a composite graph of signals near the Lift-off Point of Intersection to illustrate the ability to quantify material loss independently of lift-off variations for a driver pickup transducer.

The possibility to quantitatively determine the loss of material due to corrosion is not readily apparent with FIG. 5. However, the Lift-off Point of Intersection also provides the ability to quantify the amount of material loss in a multi-layer structure. The same type of testing was carried out as previously done with a single coil transducer. The balanced transient responses obtained are shown in FIG. 6, and demonstrate the ability to quantitatively evaluate the amount of corrosion (or material loss) by using a calibration specimen to ascertain the voltage amplitude associated with a given loss of material.

Various modifications may be made to the preferred embodiments of the invention without departing from the spirit and scope of the invention as defined in the appended claims.

What is claimed is:

1. A method for detecting defects in a metallic structure, the method comprising locating a transducer at a first distance from said metal structure at one area that lacks any significant defects in the structure, activating said transducer with a square wave voltage-controlled excitation to generate eddy currents in the structure and then sensing, with at least one magnetic flux sensor, time-varying magnetic fields generated by the transducer and said eddy currents, signals obtained from said at least one sensor being recorded, this process being repeated to obtain at least one other recorded signal that is obtained with the transducer being located in the same location but at a different lift-off distance from said one area, determining where the recorded signals cross to establish a Lift-off Point of Intersection at a point in time, placing said transducer at other areas of said structure which are to be tested for defects, activating said transducer with similar voltage-controlled excitation as applied at said one area, then obtaining and recording signals sensed from the time-varying magnetic fields generated by the transducer and eddy currents in a similar manner as at said one area, comparing the recorded signals amplitudes which are obtained at said other areas at said point in time with those of signals obtained at said one area wherein differences in signal amplitude provides indications of any defects present and a quantitative evaluation of such defects at areas being tested.

2. A method as defined in claim 1, wherein at least three recorded signals are obtained with the transducer being located at different distances from said one area.

3. A method as defined in claim 2, wherein one recorded signal is obtained at each of said other areas of said structure.

4. A method as defined in claim 1, wherein said transducer and said at least one magnetic flux sensor is a single coil.

5. A method as defined in claim 2, wherein said transducer and said at least one magnetic flux sensor is a single coil.

6. A method as defined in claim 3, wherein said transducer and said at least one magnetic flux sensor is a single coil.

7. A method as defined in claim 1, wherein said transducer comprises separate coils, one being used as a field source and another coil being said at least one magnetic flux sensor used exclusively to sense the rate of change of the total magnetic flux.

8. A method as defined in claim 2, wherein said transducer comprises separate coils, one being used as a field source and another coil being said at least one magnetic flux sensor used exclusively to sense the rate of change of the total magnetic flux.

9. A method as defined in claim 3, wherein said transducer comprises separate coils, one being used as a field source and another coil being said at least one magnetic flux sensor used exclusively to sense the rate of change of the total magnetic flux.

10. A method for detecting the material loss due to corrosion in a multi-layer metal structure comprising placing a transducer near said metal structure at one area that lacks any significant defects, activating said transducer with a square wave voltage-controlled excitation to generate eddy currents in said structure and then sensing the magnetic flux generated by the transducer and said eddy currents with transient signals thereby obtained being recorded, placing said transducer at said one area but at a different distance from said structure and activating the transducer with a similar voltage-controlled excitation to again generate eddy currents whose magnetic flux are sensed together with the transducer produced flux, signals obtained from the sensed flux being recorded, determining where the recorded signals cross to establish a Lift-off Point of Intersection at a point in time, placing said transducer at other areas of said structure which are to be tested for corrosion, activating said transducer with similar voltage-controlled excitation and obtaining and recording signals sensed from the magnetic flux generated by eddy currents and the transducer in a similar manner as at said one area, comparing the recorded signals amplitude which was obtained at each of said other areas at said point in time with those of signals obtained at said one area whereby differences in recorded signal amplitude provide an indication of any corrosion being present at an area being tested and a quantitative evaluation of the material loss due to corrosion.

11. A method as defined in claim 10, wherein at least three recorded signals are obtained with the transducer being located at different distances from said one area.

12. A method as defined in claim 11, wherein one recorded signal is obtained at each of said other areas of said structure.

13. A method as defined in claim 10, wherein said transducer and said at least one magnetic flux sensor is a single coil.

14. A method as defined in claim 11, wherein said transducer and said at least one magnetic flux sensor is a single coil.

15. A method as defined in claim 12, wherein said transducer and said at least one magnetic flux sensor is a single coil.

16. A method as defined in claim 10, wherein said transducer comprises separate coils, one being used as a field source and another coil being said at least one magnetic flux sensor used exclusively to sense the rate of change of the total magnetic flux.

17. A method as defined in claim 11, wherein said transducer comprises separate coils, one being used as a field source and another coil being said at least one magnetic flux sensor used exclusively to sense the rate of change of the total magnetic flux.

18. A method as defined in claim 12, wherein said transducer comprises separate coils, one being used as a field source and another coil being said at least one magnetic flux sensor used exclusively to sense the rate of change of the total magnetic flux.

* * * * *

UNITED STATES PATENT AND TRADEMARK OFFICE
CERTIFICATE OF CORRECTION

PATENT NO. : 6,344,741 B1
DATED : February 5, 2002
INVENTOR(S) : Giguere et al.

It is certified that error appears in the above-identified patent and that said Letters Patent is hereby corrected as shown below:

<u>Column 6,</u>
Line 24, change to read as follows:
-- Intersection. That time will be the same for any Lift-off <u>Point of Intersection for responses recorded at other areas of</u> the --.

Signed and Sealed this

Fourth Day of June, 2002

*Attest:*

*Attesting Officer*

JAMES E. ROGAN
*Director of the United States Patent and Trademark Office*